United States Patent [19]

Bondinell et al.

[11] Patent Number: 4,707,483

[45] Date of Patent: Nov. 17, 1987

[54] 1-PHENYL-3-BENZAZEPINES AND THEIR USE FOR TREATING GASTROINTESTINAL MOTILITY DISORDERS

[75] Inventors: William E. Bondinell, Wayne; Thomas Wen-Fu Ku, Dresher; Herbert S. Ormsbee, III, Wayne, all of Pa.

[73] Assignee: Smithkline Beckman Corporation, Philadelphia, Pa.

[21] Appl. No.: 811,790

[22] Filed: Dec. 20, 1985

[51] Int. Cl.$^4$ .................... A61K 31/55; C07D 223/16
[52] U.S. Cl. ..................................... 514/273; 540/595
[58] Field of Search ................. 260/239 BB; 514/273; 540/595

[56] References Cited

U.S. PATENT DOCUMENTS

| | | | |
|---|---|---|---|
| 3,393,192 | 7/1968 | Walter et al. ........................ | 540/595 |
| 3,496,166 | 2/1970 | Mull et al. ........................... | 544/595 |
| 4,104,379 | 8/1978 | Gallagher et al. .................. | 514/213 |
| 4,206,210 | 6/1980 | Holden ................................ | 514/216 |
| 4,265,890 | 5/1981 | Holden et al. ...................... | 514/213 |
| 4,284,556 | 8/1981 | Holden et al. ...................... | 540/349 |
| 4,514,394 | 4/1985 | Chambers et al. .................. | 514/213 |

FOREIGN PATENT DOCUMENTS

WO85/00808  2/1985  PCT Int'l Appl. .
1268243  3/1972  United Kingdom .

Primary Examiner—Robert T. Bond
Assistant Examiner—D. B. Springer
Attorney, Agent, or Firm—Linda E. Hall; Stuart R. Suter; Alan D. Lourie

[57] ABSTRACT

1-Phenyl-3-benzazepine compounds are useful in treating gastrointestinal motility disorders. A particular compound of this invention is 8-hydroxy-3-methyl-1-phenyl-7-phenylthio-2,3,4,5-tetrahydro-1H-3-benzazepine.

10 Claims, No Drawings

1-PHENYL-3-BENZAZEPINES AND THEIR USE FOR TREATING GASTROINTESTINAL MOTILITY DISORDERS

This invention relates to new 1-phenyl-3-benzazepine compounds, pharmaceutical compositions containing them and methods of treating gastrointestinal motility disorders by administering these compounds.

The compounds of this invention have utility in the treatment of gastrointestinal diseases, in particular gastrointestinal motility disorders. The compounds are useful therapeutically for gastroesophageal reflux disease and disorders of delayed gastric emptying of various etiologies including diabetes, surgery, and idiopathic delayed emptying. The compounds may also be useful in treating disorders of upper GI motility, aspiration, early satiety, anorexia nervosa, and in diagnostic radiology or to facilitate intubation.

The compounds of this invention are represented by the following formula (I):

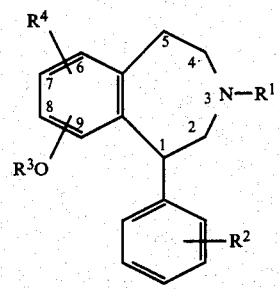

in which:
$R^1$ is hydrogen, lower alkyl or $C_3$–$C_5$ alkenyl;
$R^2$ is hydrogen, hydroxy, lower alkoxy, halogen, trifluoromethyl, lower alkyl, $SO_n$lower alkyl, $SO_nCF_3$, $SO_n$phenyl or $SO_2NR^6R^7$;
$R^3$ is hydrogen, lower alkyl or lower alkanoyl;
$R^4$ is $SO_nR^5$ or $SO_2NR^6R^7$;
n is 0, 1 or 2;
$R^5$ is:

or trifluoromethyl; and
$R^6$ and $R^7$ are hydrogen or lower alkyl or a pharmaceutically acceptable acid addition salt thereof.

Particular compounds of formula (I) are those in which $R^3O$ is in the 8-position. Further particular compounds of formula (I) are those in which $R^3O$ is in the 8-position and $R^4$ is in the 7-position.

A group of compounds of formula (I) is that in which $R^4$ is $SO_nR^5$ or $SO_2NH_2$, $R^3$ is hydrogen, $R^1$ is hydrogen or methyl and $R^2$ is hydrogen, hydroxy, $SO_n$lower alkyl, $SO_nCF_3$, $SO_n$phenyl or $SO_2NR^6R^7$, and, in addition, $R^4$ may be in the 7-position and $R^3O$ may be in the 8-position.

Specific compounds of this invention are:
8-hydroxy-3-methyl-1-phenyl-7phenylthio-2,3,4,5-tetrahydro-1H-3-benzazepine
8-hydroxy-1-phenyl-7-trifluoromethylsulfonyl-2,3,4,5-tetrahydro-1H-3-benzazepine
8-hydroxy-1-phenyl-7-sulfamoyl-2,3,4,5-tetrahydro-1H-3-benzazepine.

The compounds of this invention are optically active and exist as racemates and as (R) and (S) enantiomers. Resolution of the optical isomers may be accomplished by standard procedures such as fractional crystallization of their salts with opically active acids from appropriate solvents. This invention includes all isomers whether separated or mixtures thereof.

The compounds of formula (I) are prepared as follows:

Procedure A

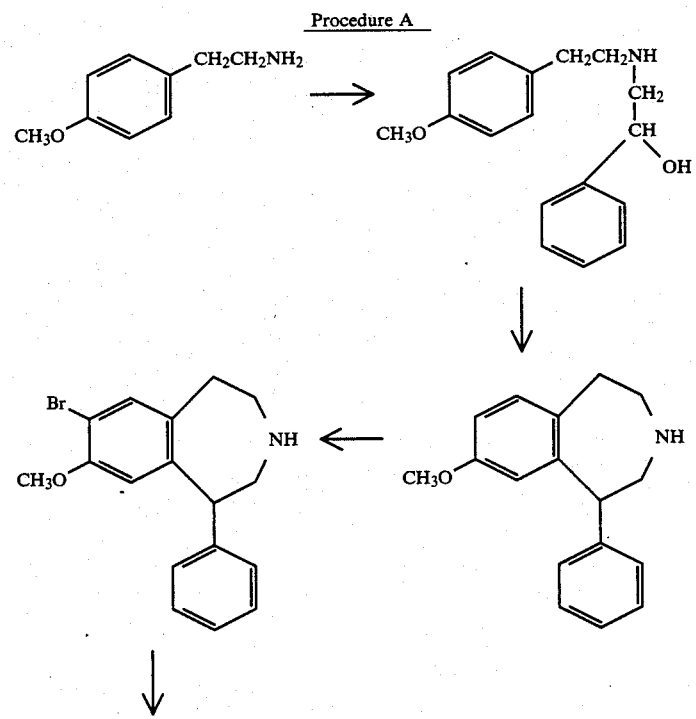

-continued
Procedure A
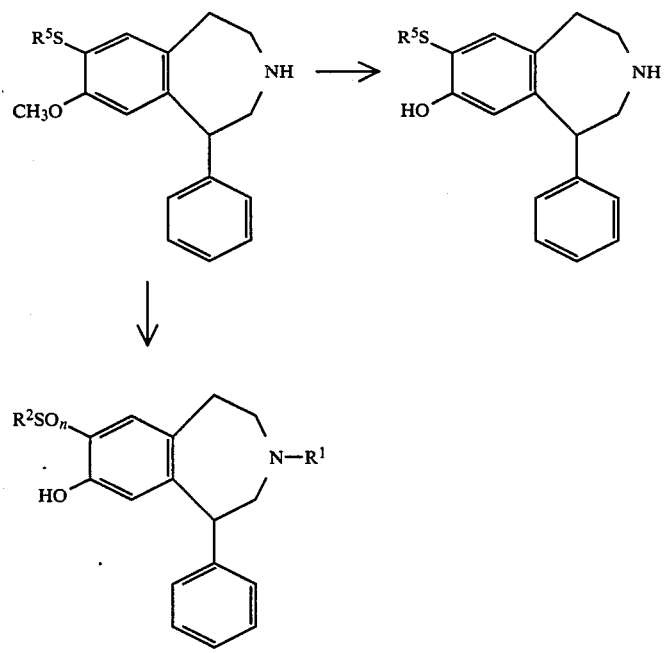
Procedure B
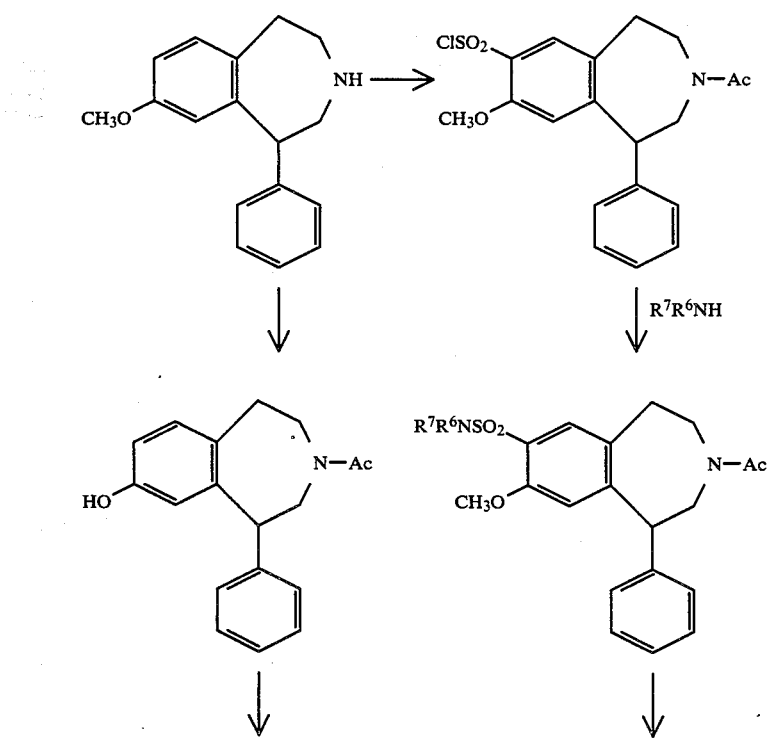

Procedure B

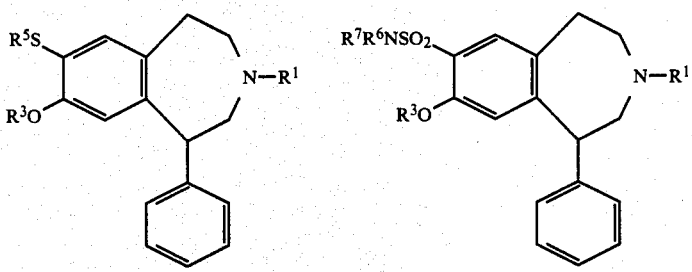

According to the Procedure A above, 4-methoxyphenethylamine is reacted with styrene oxide and the resulting N-(2-hydroxy-2-phenyl)ethyl-4-methoxyphenethylamine is cyclized with acid to give 8-methoxy1-phenyl-2,3,4,5-tetrahydro-1H-3-benzazepine. A salt, for example the hydrochloride, of this compound is reacted with bromine to give the 7-bromo compound which is reacted with butyllithium and phenyl disulfide or trifluoromethanesulfenyl chloride to give 8-methoxy-1-phenyl-7-phenylthio(or 7-trifluoromethylthio)-2,3,4,5-tetrahydro-1H-3-benzazepine. The 8-hydroxy compounds are prepared by O-demethylating the 8-methoxy compounds by standard procedures.

The phenylthio and trifluoromethylthio compounds are oxidized by protecting the nitrogen in the benzazepine ring, for example with an acyl group, then treating with an oxidizing agent such as hydrogen peroxide or a peracid such as 3-chloroperbenzoic acid. One equivalent of the oxidizing agent gives the sulfinyl compounds and two equivalents gives the sulfonyl compounds.

The oxizidized compounds are then deacylated and optionally N-alkylated, N-alkenylated, O-demethylated, O-alkylated or O-alkanoylated. These procedures are carried out by standard methods and may be carried out in various order of steps to prepare the desired compounds.

According to Procedure B, 8-methoxy-1-phenyl-2,3,4,5-tetrahydro-1H-3-benzazepine is acylated at the nitrogen atom using an acylating agent such as acetic anhydride and the resulting N-acyl compound is reacted with chlorosulfonic acid and then with thionyl chloride to give 3-acyl-7-chlorosulfonyl-8-methoxy-1-phenyl-2,3,4,5-tetrahydro-1H-3-benzazepine.

The 3-acyl-7-chlorosulfonyl-8-methoxy-1-phenyl-2,3,4,5-tetrahydro-1H-3-benzazepine is reacted with an amine ($R^7R^6NH$) to give the 7-sulfamoyl compounds. When $R^7$ and $R^6$ are hydrogen, preferably ammonium hydroxide is used.

Also according to Procedure B, 8-methoxy-1-phenyl-2,3,4,5-tetrahydro-1H-3-benzazepine is N-acylated, O-demethylated and reacted with a sulfenyl chloride to give 3-acyl-8-hydroxy-7-phenylthio(or 7-trifluoromethylthio)-1-phenyl-2,3,4,5-tetrahydro-1H-3-benzazepines.

The compounds of formula (I) where $R^4$ and $OR^3$ are in positions other than the 7 and 8 positions, respectively, are prepared by similar procedures from the corresponding 1-phenyl-methoxy-2,3,4,5-tetrahydro-1H-3-benzazepine intermediates by inserting bromo, or chlorosulfonyl, phenylthio or trifluoromethylthio and carrying out the above described procedures.

The compounds of formula (I) where $R^2$ is other than hydrogen are prepared from an appropriately substituted styrene oxide to give the 1-(substituted phenyl)-methoxy-2,3,4,5-tetrahydro-1H-3-benzazepine intermediate which is then reacted according to Procedure A or B described hereabove.

The compounds of formula (I) form pharmaceutically acceptable acid addition salts with organic or inorganic acids. Examples of these acids are hydrochloric, hydrobromic, sulfuric, phosphoric, acetic, tartaric, citric, maleic, lactic, oxalic, succinic, methanesulfonic, and benzenesulfonic acids. The salts are formed according to methods known to the art. If the product is isolated as an acid addition salt, it may be treated with an inorganic or organic base, such as aqueous sodium hydroxide, sodium carbonate, triethylamine, etc., and converted to the corresponding free base. The base can then be treated with an appropriate acid, for example in an aqueous miscible solvent, such as a lower alkanol preferably methanol or ethanol, to give the desired salt.

The effect of the pharmacologically active compounds of this invention on gastrointestinal motility is demonstrated in test procedures as follows:

(1) an increase in resting pressure of the lower esophageal sphincter (LES) in dogs; and (2) an increase in the rate of gastric emptying in rats.

Method for Determination of LES Pressure in the Anesthetized Dog

Mongrel or beagle dogs, male and female, are anesthetized using sodium pentobarbital (35.0 mg/kg., i.v.). Sodium pentobarbital is then continuously infused (approximately 6.0 mg/kg/hr) to maintain deep anesthesia. Blood pressure is monitored via a catheter surgically implanted into the femoral artery and attached to a Gould-Statham P23ID transducer. A catheter is also implanted into the femoral vein to administer test drugs. Respiration is maintained by an endotracheal tube attached to a respirator. A continuously perfused manometric catheter system including a Dent sleeve to measure sphincter pressure (Dent, *Gastroenterology* 71: 263–267, 1976) is inserted into the esophagus and positioned so that intraluminal pressure is recorded from the body of the esophagus, the lower esophageal sphincter (LES) and the fundus of the stomach. The Dent sleeve catheter is perfused at a rate of 0.5 ml of water per minute for each lumen of the catheter by using an Arndorfer Hydraulic Capillary Infusion System. A cannula is implanted into the gastric antrum to allow drainage of the perfusate solution and prevent intestinal distension. Continuous tracings of esophageal, LES and fundus pressure are monitored on a Grass Polygraph (Model 7D). Correct positioning of the Dent sleeve is verified by noting a high pressure zone at the LES and by administration of an intravenous dose of 5-HT (usually 10–15 mcg/kg) which contracts the LES while having little or no recordable effect on either the body of the esophagus or the fundus. After verification of placement of the sleeve, the animal is allowed to stabilize for approximately 30 minutes.

Compounds are administered intravenously or intraduodenally. In most cases, succeeding doses of the same or different compounds are given only after the LES pressure has returned to approximate pre-dosing baseline values. In all cases, the magnitude of change in LES pressure is determined from the baseline pressure immediately prior to each treatment to the maximum pressure during treatment. Since the compounds used usually produce an immediate effect of LES pressure, no pretreatment time prior to measurement is necessary during this testing.

Direct assay techniques are used to estimate an Effective Dose 20 ($ED_{20}$) for the test compound in individual animals. The mean $ED_{20}$ and 95% confidence limits are determined using the individual $ED_{20}$ values from a group of animals ($N = \geq 3$) that received the same treatment. The $ED_{20}$ is the dose which increases LES pressure 20 mm Hg. The $ED_{20}$ of the 8-hydroxy-7phenylthio compound of Example 1 is 20 mcg/kg, i.v.

Gastric Emptying in the Rat

Fasted rats are administered 0.5 $\mu$Ci of $NA_2{}^{51}CrO_4$ (0.2 ml vol) into the stomach with an oral feeding tube. Compounds for evaluation or vehicle controls are administered either 15 minutes before (oral administration) or simultaneously with (intravenous administration) the test meal. After 35 minutes the rats are killed by cervical dislocation and the stomach is removed. Gastric emptying is measured from the amount of $^{51}Cr$ remaining in the stomach at death. The rate of gastric emptying as compared to control is determined.

This invention also includes pharmaceutical compositions for treatment of gastrointestinal motility disorders comprising a compound of formula (I) or a pharmaceutically acceptable acid addition salt thereof and a pharmaceutically acceptable carrier.

The pharmacologically active compounds of formula (I) can be administered orally or parenterally. Preferably, these compounds are administered in conventional dosage unit forms prepared by combining an appropriate dose of the compound with standard pharmaceutical carriers. The dosage units will contain the active ingredient in an effective amount selected from about 5 mg. to about 250 mg., preferably 10 mg. to 100 mg.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent can include any time delay material well known to the art, such as glyceryl monostearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a trouche or lozenge. The amount of solid carrier will vary widely but preferably will be from about 25 mg. to about 1 g. If a liquid carrier is used, the preparation will be in the form of a syrup, emulsion, soft gelatin capsule, sterile injectable liquid such as an ampul or an aqueous or nonaqueous liquid suspension.

The pharmaceutical compositions are prepared by conventional techniques involving procedures such as mixing, granulating and compressing when necessary or variously mixing and dissolving the ingredients as appropriate to the desired composition.

The method of treating gastrbintestinal motility disorders in accordance with this invention comprises administering internally to a subject in need of said treatment an effective amount of a compound of formula (I) or a pharmaceutically acceptable acid addition salt thereof.

The compound will preferably be administered in a dosage unit form orally or parenterally. Advantageously, equal doses will be administered one to four times daily with the daily dosage regimen being from about 5 mg. to about 1000 mg., preferably from 10 mg. to 400 mg. The method described above is useful for treating gastrointestinal motility disorders.

One skilled in the art will recognize that in determining the amounts of the compound needed to produce the desired pharmacological effect without toxic side effects, the activity of the particular compound as well as the size of the host animal must be considered.

The following examples illustrate the invention but are not to be construed as limiting the scope thereof. Temperatures are in degrees Centigrade unless otherwise stated.

EXAMPLE 1

4-Methoxyphenethylamine (148 g, 0.98 m) and styrene oxide (118 g, 0.98 m) were stirred and heated to 95° for 16 hours. The mixture was poured into 3:1 hexaneethyl acetate (600 ml), diluted with hexane and the resulting solid obtained by filtration to give N-[1-(2-hydroxy-2-phenyl)ethyl]-4-methoxyphenethylamine.

The amine (106 g, 0.39 m) was refluxed in a mixture of trifluoroacetic acid (1.2 l) and concentrated sulfuric acid (30 ml, 0.57 m) for 2 hours. The trifluoroacetic acid was evaporated in vacuo and the residue poured into ice water (1.2 l). The solution was made alkaline with 40% aqueous sodium hydroxide and extracted with ethyl acetate. The ethyl acetate solution was acidified with hydrogen chloride gas to give 8-methoxy-1-phenyl-2,3,4,5-tetrahydro-1H-3-benzazepine hydrochloride, m.p. 224°–234°.

8-Methoxy-1-phenyl-2,3,4,5-tetrahydro-1H3-benzazepine hydrochloride (66 g, 0.23 m) was suspended in acetic acid (300 ml) and treated with bromine (43 g, 0.27 m). The mixture was heated to 95° for one hour, cooled and filtered. The filter cake was partitioned between ethyl acetate and ammonium hydroxide to afford 7-bromo-8-methoxy-1-phenyl-2,3,4,5-tetrahydro-1H-3-benzazepine.

7-Bromo-8-methoxy-1-phenyl-2,3,4,5-tetrahydro-1H-3-benzazepine (9.6 g, 0.03 m), 37% formalin (27 ml) and 95% formic acid (38 ml) were mixed and heated to reflux for 16 hours. The mixture was concentrated in vacuo, treated with 10% hydrochloric acid (70 ml) and concentrated in vacuo. The residue was partitioned between ethyl acetate and ammonium hydroxide to give 7-bromo8-methoxy-3-methyl-1-phenyl-2,3,4,5-tetrahydro-1H-3-benzazepine.

7-Bromo-8-methoxy-3-methyl-1-phenyl-2,3,4,5-tetrahydro-1H-3-benzazepine (12.8 g, 0.037 m) dissolved in ether (70 ml) was added to a mixture of 2.5N butyllithium in hexane (80 ml) and ether (80 ml) stirred at −70°. After thirty minutes, phenyl disulfide (40 g, 0.18 m) dissolved in ether (200 ml) was added slowly. The mixture was stirred for 16 hours, poured into a mixture of ice and concentrated hydrochloric acid (100 ml) and stirred. The mixture was filtered and the filter cake was recrystallized from methanol-ether to qive 8-methoxy-3-methyl-1-phenyl-7-phenylthio-2,3,4,5-tetrahydro-1H-3-benzazepine hydrochloride.

8-Methoxy-3-methyl-1-phenyl-7-phenylthio-2,3,4,5-tetrahydro-1H-3-benzazepine hydrochloride (4.5 g, 0.011 m) dissolved in methanesulfonic acid (165 ml) was treated with methionine (8.3 g, 0.055 m) and stirred for 16 hours at 25° C. The mixture was poured into ice water, basified with ammonium hydroxide and extracted with ethyl acetate. The organic phase was concentrated in vacuo and the residue purified by chromatography on silica eluted with methanol-methylene chloride (1:50) to give 8-hydroxy-3-methyl-1-phenyl-7-phenylthio-2,3,4,5-tetrahydro-1H-3-benzepine which was treated with hydrooen chloride to give 8-hydroxy-3-methyl-1-phenyl-7-phenylthio-2,3,4,5-tetrahydro-1H-3-benzazepine hydrochloride, m.p. 175° C.

EXAMPLE 2

A mixture of 8-methoxy-1-phenyl-2,3,4,5-tetrahydro-1H-3-benzazepine hydrochloride (20 g, 0.07 m), sodium acetate (5 g, 0.07 m), and acetic anhydride (100 ml) was stirred for 16 hours and concentrated in vacuo.

The residue was stirred with aqueous sodium carbonate and extracted with methylene chloride. The methylene chloride phase was washed with dilute hydrochloric acid, with water, dried over sodium sulfate and concentrated in vacuo to give 3-acetyl-8-methoxy-1-phenyl-2,3,4,5-tetrahydro-1H-3-benzazepine.

Chlorosulfonic acid (2.3 g, 0.02 m) dissolved in methylene chloride (50 ml) was added slowly to a solution of 3-acetyl-8-methoxy-1-phenyl-2,3,4,5-tetrahydro-1H-3-benzazepine (2.95 g, 0.01 m) in methylene chloride (100 ml) stirred at −20°. The mixture was stirred at −20° for thirty minutes, and allowed to warm to 25°. The methylene chloride was decanted and the insoluble residue was treated with excess thionyl chloride in chloroform, heated to reflux, cooled and poured into ice water. The mixture was extracted with chloroform and the organic layer was washed, dried with sodium sulfate and concentrated in vacuo to give 3-acetyl 7-chlorosulfonyl-8-methoxy-1-phenyl-2,3,4,5-tetrahydro-1H-3-benzazepine.

3-Acetyl-7-chlorosulfonyl-8-methoxy-1-phenyl-2,3,4,5-tetrahydro-1H-3-benzazepine (3.9 g, 0.01 m) is dissolved in methylene chloride (50 ml) and added to concentrated ammonium hydroxide (15 ml), then stirred and filtered to give 3-acetyl-8-methoxy-1-phenyl-7-sulfamoyl-2,3,4,5-tetrahydro-1H-3-benzazepine.

The sulfamoyl compound (3.7 g, 0.01 m) is suspended in 3N hydrochloric acid, heated to reflux for 16 hours and concentrated in vacuo to give 8-methoxy-1-phenyl-7-sulfamoyl-2,3,4,5-tetrahydro-1H-3-benzazepine hydrochloride. 8-Methoxy-1-phenyl-7-sulfamoyl-2,3,4,5-tetrahydro-1H-3-benzazepine hydrochloride (3.7 g, 0.01 m) is dissolved in 48% hydrobromic acid (20 ml), refluxed for 2 hours and concentrated in vacuo to afford 8-hydroxy-1-phenyl-7-sulfamoyl-2,3,4,5-tetrahydro-1H-3-benzazepine hydrobromide.

EXAMPLE 3

Following the general procedure of Example 2, 3-acetyl-7-chlorosulfonyl-8-methoxy-1-phenyl-2,3,4,5-tetrahydro-1H-3-benzazepine is treated with methylamine and then with refluxing hydrochloric acid to give 8-methoxy-7-(N-methylsulfamoyl)-1-phenyl-2,3,4,5-tetrahydro-1H-3-benzazepine hydrochloride. By the procedure of Example 2, the methoxy compound is treated with hydrobromic acid to afford 8-hydroxy-7 (N-methylsulfamoyl)-1-phenyl-2,3,4,5-tetrahydro-1H-3-benzazepine hydrobromide.

EXAMPLE 4

3-Acetyl-7-chlorosulfonyl-8-methoxy-1-phenyl-2,3,4,5-tetrahydro-1H-3-benzazepine is treated with dimethylamine and then with refluxing hydrochloric acid to give 8-methoxy-7-(N,N-dimethylsulfamoyl)-1-phenyl-2,3,4,5-tetrahydro-1H-3-benzazepine hydrochloride.

Treating the 8-methoxy compound with hydrobromic acid by the procedure of Example 2 gives 8-hydroxy-7-(N,N-dimethylsulfamoyl)-1-phenyl-2,3,4,5-tetrahydro-1H-3-benzazepine hydrobromide.

EXAMPLE 5

A mixture of 3-methoxyphenethylamine (6.1 g, 0.04 m) and styrene oxide (4.9 g, 0.04 m) was stirred and heated to 95° for 16 hours. The mixture was treated with n-butyl chloride to give N-[1-(2-hydroxy-2-phenyl)ethyl]-3-methoxyphenethylamine, m.p. 86°–88°.

N-[1-(2-Hydroxy-2-phenyl)ethyl]-3-methoxyphenethylamine (2 g, 7 mmol) dissolved in trifluoroacetic acid (20 ml) and concentrated sulfuric acid (2 ml) was refluxed for 2 hours and concentrated in vacuo. The residue was basified with 10% aqueous sodium hydroxide and extracted into ethyl acetate. The ethvl acetate was washed with water and with brine, dried over magnesium sulfate and concentrated in vacuo. The residue was dissolved in acetonitrile and treated with maleic acid to give 7-methoxy-1-phenyl-2,3,4,5-tetrahydro-1H-3-benzazepine maleate, m.p. 165°–167°.

Following the general procedure of Example 2, 7-methoxy-1-phenyl-2,3,4,5-tetrahydro-1H-3-benzazepine maleate is acetylated and treated with chlorosulfonic acid followed by thionyl chloride to give 3-acetyl-8-chlorosulfonyl-7-methoxy-1-phenyl-2,3,4,5-tetrahydro-1H-3-benzazepine.

By the procedure of Example 2, 3-acetyl-8-chlorosulfonyl-7-methoxy-1-phenyl-2,3,4,5-tetrahydro-1H-3-benzazepine is treated with ammonium hydroxide followed by hydrochloric acid to give 7-methoxy-1-phenyl-8-sulfamoyl-2,3,4,5-tetrahydro-1H-3-benzazepine hydrochloride.

7-Methoxy-1-phenyl-8-sulfamoyl-2,3,4,5-tetrahydro-1H-3-benzazepine hydrochloride is treated with hydrobromic acid by the procedure of Example 2 to give 7-hydroxy-1-phenyl-8-sulfamoyl-2,3,4,5-tetrahydro-1H-3-benzazepine hydrobromide.

EXAMPLE 6

Following the general procedure of Example 2, 3-acetyl-8-chlorosulfonyl-7-methoxy-1-phenyl-2,3,4,5-tetrahydro-1H-3-benzazepine is treated with methylamine and then with refluxing hydrochloric acid to afford 7-methoxy-8-(N-methylsulfamoyl)-1-phenyl-2,3,4,5-tetrahydro-1H-3-benzazepine hydrochloride and the methoxy compound is treated with refluxing hydrobromic acid to give 7-hydroxy-8-(N-methylsulfamoyl)-1-phenyl-2,3,4,5-tetrahydro-1H-3-benzazepine hydrobromide.

EXAMPLE 7

Reacting 3-acetyl-8-chlorosulfonyl-7-methoxy-1-phenyl-2,3,4,5-tetrahydro-1H-3-benzazepine with dimethylamine and then with refluxing hydrochloric acid gives 7-methoxy-8-(N,N-dimethylsulfamoyl)-1-phenyl-2,3,4,5-tetrahydro-1H-3-benzazepine hydrochloride. Treating this methoxy compound with refluxing hydrobromic acid gives 7-hydroxy-8-(N,N-dimethylsulfamoyl)-1-phenyl-2,3,4,5-tetrahydro-1H-3-benzazepine hydrobromide.

EXAMPLE 8

A solution of 3-acetyl-8-methoxy-1-phenyl-2,3,4,5-tetrahydro-1H-3-benzazepine (13 g, 0.01 m) in methylene chloride (50 ml) stirred at 5° was treated with chlorosulfonic acid (11.6 g, 0.1 m). The mixture was stirred at 25° for 2 hours, poured into ice water and extracted with chloroform. The chloroform extract was washed, dried with sodium sulfate and concentrated in vacuo to give 3-acetyl-7-chlorosulfonyl-1-[4-(chlorosulfonyl)phenyl]-8-methoxy-2,3,4,5-tetrahydro-1H-3-benzazepine.

By the procedure of Example 2, 3-acetyl-7-chlorosulfonyl-1-[4-(chlorosulfonyl)phenyl]-8-methoxy-2,3,4,5-tetrahydro-1H-3-benzazepine is treated with ammonium hydroxide and then with refluxing hydrochloric acid to give 8-methoxy-7-sulfamoyl-1-[4-(sulfamoyl)phenyl]-2,3,4,5-tetrahydro-1H-3-benzazepine hydrochloride.

The methoxy compound is treated with hydrobromic acid by the procedure of Example 2 to give 8-hydroxy-7-sulfamoyl-1-[4-(sulfamoyl)phenyl]-2,3,4,5-tetrahydro-1H-3-benzazepine hydrobromide.

EXAMPLE 9

Following the general procedure of Example 1, 7-bromo-8-methoxy-1-phenyl-2,3,4,5-tetrahydro-1H-3benzazepine dissolved in toluene is treated with n-butyl lithium and then with trifluoromethanesulfenyl chloride to give 8-methoxy-1-phenyl-7-trifluoromethylthio-2,3,4,5-tetrahydro-1H-3-benzazepine.

8-Methoxy-1-phenyl-7-trifluoromethylthio-2,3,4,5-tetrahydro-1H-3-benzazepine in methanesulfonic acid is treated with methionine to give 8-hydroxy-1-phenyl-7-trifluoromethylthio-2,3,4,5-tetrahydro 1H-benzazepine.

EXAMPLE 10

8-Methoxy-1-phenyl-7-trifluoromethylthio-2,3,4,5-tetrahydro-1H-3-benzazepine (3.7 g, 0.01 m) dissolved in methylene chloride is treated with trifluoroacetic anhydride (2.2 g, 0.01 m) to give 8-methoxy-1-phenyl-3-trifluoroacetyl-7-trifluoromethylthio-2,3,4,5-tetrahydro-1H-3-benzazepine.

8-Methoxy-1-phenyl-3-trifluoroacetyl-7-trifluoromethylthio-2,3,4,5-tetrahydro-1H-3-benzazepine (4.7 g, 0.01 m) dissolved in acetic acid (75 ml) is treated with 30% hydrogen peroxide (20 ml) and stirred for 16 hours. The mixture is diluted with water and extracted with ether to give 8-methoxy-1-phenyl-3-trifluoroacetyl-7-trifluoromethylsulfonyl-2,3,4,5-tetrahydro-1H-3-benzazepine.

8-Methoxy-1-phenyl-3-trifluoroacetyl-7-trifluoromethylsulfonyl-2,3,4,5-tetrahydro-1H-3-benzazepine (5 g, 0.01 m) dissolved in methanol is treated with 40% aqueous sodium hydroxide and stirred. The mixture is concentrated in vacuo and partitioned between ethyl acetate and water to give 8-methoxy-1-phenyl-7-trifluoromethylsulfonyl-2,3,4,5-tetrahydro-1H-3-benzazepine.

Following the general procedure of Example 1, 8-methoxy-1-phenyl-7-trifluoromethylsulfonyl-2,3,4,5-tetrahydro-1H-3-benzazepine in methanesulfonic acid is treated with methionine to give 8-hydroxy-1-phenyl-7-trifluoromethylsulfonyl-2,3,4,5-tetrahydro-1H-3-benzazepine.

EXAMPLE 11

Following the general procedure of Example 10, 8-methoxy-1-phenyl-3-trifluoroacetyl-7-trifluoromethylthio-2,3,4,5-tetrahydro-1H-3-benzazepine is treated with one equivalent of hydrogen peroxide, then with aqueous sodium hydroxide and with methionine/methanesulfonic acid to give 8-hydroxy-1-phenyl-7-trifluoromethylsulfinyl-2,3,4,5-tetrahydro-1H-3-benzazepine.

EXAMPLE 12

4-Bromo-3-methoxybenzoic acid (23.1 g, 0.1 m) dissolved in tetrahydrofuran (200 ml) is added to 1M borane in tetrahydrofuran (150 ml) stirred at 5°. The mixture is refluxed, cooled, treated with methanol, refluxed and concentrated in vacuo to give 4-bromo-3-methoxybenzyl alcohol.

4-Bromo-3-methoxybenzyl alcohol (21.7 g, 0.1 m) dissolved in toluene (200 ml) containing pyridine (11.8 g, 0.15 m) is stirred at 5° and treated wiih thionyl chloride (23.8 g, 0.2 m). The mixture is stirred, diluted with water and the organic layer washed with dilute hydrochloric acid, dried and concentrated in vacuo to give 4-bromo-3-methoxybenzyl chloride.

4-Bromo-3-methoxybenzyl chloride (23.5 g, 0.1 m) dissolved in ethanol (500 ml) is treated with potassium cyanide (13 g, 0.2 m) dissolved in water. The mixture is warmed and stirred to give 4-bromo-3-methoxyphenylacetonitrile.

4-Bromo-3-methoxyphenylacetonitrile (22.6 g, 0.1 m) dissolved in tetrahydrofuran (100 ml) is added to 1M borane in tetrahydrofuran (300 ml) stirred at 25°. The mixture is refluxed, cooled to 0° and treated cautiously with 2N hydrochloric acid to give 4-bromo-3-methoxyphenethylamine.

Following the general procedure of Example 5, 4-bromo-3-methoxyphenethylamine (2.3 g, 0.1 m) is treated with 4-methoxystyrene oxide (15 g, 0.1 m) to give N-[1-[2-hydroxy-2-(4-methoxyphenyl)]ethyl]-4-bromo-3-methoxyphenethylamine. This N-substituted 4-bromo-3-methoxyphenethylamine (3.8 g, 0.01 m) is refluxed in a mixture of trifluoroacetic acid (20 ml) and sulfuric acid (20 ml) to give 8-bromo-7-methoxy-1-(4-methoxyphenyl)-2,3,4,5-tetrahydro-1H-3-benzazepine.

Following the general procedure of Example 1, the bromo compound (3.6 g, 0.01 m) is reacted with n-butyl lithium in ether and then with benzyl disulfide to give 8-benzylthio-7-methoxy-1-(4-methoxyphenyl)-2,3,4,5-tetrahydro-1H-3-benzazepine.

The benzylthio-benzazepine (4 g, 0.01 m) is dissolved in acetone (50 ml) and water (10 ml). The solution is treated with sodium carbonate (3 g, 0.03 m) in water (5 ml), cooled and treated with benzyl chloroformate (3.4 g, 0.03 m) in acetone (15 ml) to give 3-benzyloxycarbonyl-8-benzylthio-7-methoxy-1-(4-methoxyphenyl)-2,3,4,5-tetrahydro-1H-3-benzazepine.

The benzyloxy compound (5.4 g, 0.01 m) is dissolved in acetic acid (50 ml) containing water (0.5 ml), stirred, cooled and treated with chlorine to give 3-benzyloxycarbonyl-8-chlorosulfonyl-7-methoxy-1-(4-methoxyphenyl)-2,3,4,5-tetrahydro-1H-3-benzazepine.

Following the general procedure of Example 2, the chlorosulfonyl compound (5.2 g, 0.01 m) is treated with ammonium hydroxide to give 3-benzyloxycarbonyl-7- methoxy-1-(4-methoxyphenyl)-8-sulfamoyl-2,3,4,5-tetrahydro-1H-3-benzazepine.

The sulfamoyl compound (5.1 g, 0.01 m) is dissolved in methylene chloride (180 ml), cooled to −15° and treated with boron tribromide (5 g, 0.02 m) in methylene chloride. The mixture is stirred at 25°, cooled and treated with methanol to give 7-hydroxy-1-(4-hydroxyphenyl)-8-sulfamoyl-2,3,4,5-tetrahydro-1H-3-benzazepine hydrobromide.

EXAMPLE 13

Following the general procedure of Example 1, 4-methoxyphenethylamine (15 g, 0.1 m) is reacted with 3-(methylthio)styrene oxide (17 g, 0.1 m) to give N-[1[2-hydroxy-2-[(3-methylthio)phenyl]]ethyl]-4-methoxyphenethylamine.

The amine (32 g, 0.1 m) is refluxed in a mixture of trifluoroacetic acid (300 ml) and sulfuric acid (8 ml) to give 8-methoxy-1-[(3-methylthio)phenyl]-2,3,4,5-tetrahydro-1H-3-benzazepine.

The 3-benzazepine (30 g, 0.1 m) is treated with acetic anhydride to give 3-acetyl-8-methoxy-1-[(3methylthio)phenyl]-2,3,4,5-tetrahydro-1H-3-benzazepine.

Following the general procedure of Example 10, the methylthiophenyl-benzazepine is heated with 30% hydrogen peroxide to give 3-acetyl-8-methoxy-1-[(3-methylsulfonyl)phenyl]-2,3,4,5-tetrahydro-1H-3-benzazepine.

The methoxy-benzazepine (3.4 g, 0.01 m) is dissolved in methanesulfonic acid (150 ml) and treated with methionine (8.2 g, 0.05 m) to give 3-acetyl-8-hydroxy-1-[(3-methylsulfonyl)phenyl]-2,3,4,5-tetrahydro-1H-3-benzazepine.

The hydroxy-benzazepine (3.3 g, 0.01 m), dissolved in carbon tetrachloride (100 ml), is treated with phenylsulfenyl chloride (2.1 g, 0.015 m) and stirred at 5°. The mixture is then stirred at 25° to give 3-acetyl-8-hydroxy-1-[(3-methylsulfonyl)phenyl]-7-phenylthio-2,3,4,5-tetrahydro-1H-3-benzazepine.

Following the general procedure of Example 2, the 3-acetyl-benzazepine is refluxed in 3N hydrochloric acid to give 8-hydroxy-1-[(3-methylsulfonyl)phenyl]7-phenylthio-2,3,4,5-tetrahydro-1H-3-benzazepine hydrochloride.

EXAMPLE 14

Following the general procedure of Example 12, 2-bromo-4-methoxybenzoic acid is converted to 2-bromo-4-methoxyphenethylamine.

Following the general procedure of Example 1, 2-bromo-4-methoxyphenethylamine (23 g, 0.1 m) is reacted with 4-chlorostyrene oxide (15 g, 0.1 m) to give N-[1[2-hydroxy-2-(4-chlorophenyl)]ethyl]-2-bromo-4-methoxyphenethylamine.

The amine (38 g, 0.1 m) is refluxed in a mixture of trifluoroacetic acid (300 ml) and sulfuric acid (8 ml) to give 6-bromo-1-(4-chlorophenyl)-8-methoxy-2,3,4,5-tetrahydro-1H-3-benzazepine.

Following the general procedure of Example 9, the bromo-benzazepine is treated with n-butyllithium and then with trifluoromethylsulfenyl chloride to give 1-(4-chlorophenyl)-8-methoxy-6-trifluoromethylthio-2,3,4,5-tetrahydro-1H-3-benzazepine.

Following the general procedure of Example 1, the methoxy-benzazepine is treated with methione and methanesulfonic acid to give 1-(4-chlorophenyl)-8-hydroxy-6-trifluoromethylthio-2,3,4,5-tetrahydro-1H-3-benzazepine.

EXAMPLE 15

By the procedures of Example 10 and 11, 8-methoxy-3-methyl-1-phenyl-7-phenylthio-2,3,4,5-tetrahydro-1H-3-benzazepine is treated with hydrogen peroxide to give the 7-phenylsulfonyl and 7-phenylsulfonyl compounds. The 8-methoxy groups are demethylated by the procedure of Example 10 to give 8-hydroxy-1-phenyl[7-phenylsulfonyl-2,3,4,5-tetrahydro-1H-3-benzazepine and the corresponding 7-phenylsulfinyl compound.

EXAMPLE 16

Using 8-methoxy-1-phenyl-2,3,4,5-tetrahydro-1H-3-benzazepine, prepared by the procedure of Example 1, in place of the corresponding 1-(3-methylthio)phenyl compound in the procedure of Example 13 provides as the product 8-hydroxy-1-phenyl-7-phenylthio-2,3,4,5-tetrahydro-1H-3-benzazepine hydrochloride.

EXAMPLE 17

Allyl bromide (1.2 g, 0.01 m) is added to a mixture of 8-hydroxy-1-phenyl-7-phenylsulfonyl-2,3,4,5-tetrahydro-1H-3-benzazepine (3.2 g, 0.01 m) and potassium carbonate (2 g) stirred in dry acetone (20 ml) at 5°. The mixture is stirred at 5°, then at 25° and is finally stirred at reflux. The mixture is poured into water, extracted with ethyl acetate and treated with ethereal hydrogen chloride to give 3-allyl-8-hydroxy-1-phenyl-7-phenylsulfonyl-2,3,4,5-tetrahydro-1H-3-benzazepine hydrochloride.

EXAMPLE 18

By the procedure of Example 1, using bis[4-(methylsulfonyl)phenyl]disulfide in place of phenyl disulfide, 8-methoxy-3-methyl-7-(4-methylsulfonyl)phenylthio-1-phenyl-2,3,4,5-tetrahydro-1H-3-benzazepine hydrochloride is prepared. This 8-methoxy compound in methanesulfonic acid is treated with methionine to give 8-hydroxy-3-methyl-7-(4-methylsulfonyl)phenylthio-1-phenyl-2,3,4,5-tetrahydro-1H-3-benzazepine hydrochloride.

EXAMPLE 19

8-Hydroxy-3-methyl-1-phenyl-1-phenylthio-2,3,4,5-tetrahydro-1H3-benzazepine hydrochloride (15 mg) is mixed with 85 mg. of lactose and 3 mg. of magnesium stearate and filled into a hard gelatin capsule.

What is claimed is:

1. A compound of the formula:

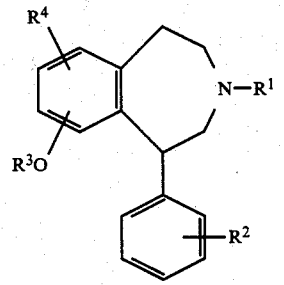

in which:
R[1] is hydrogen, lower alkyl or $C_3$–$C_5$ alkenyl;
R[2] is hydrogen, hydroxy, lower alkoxy, halogen, trifluoromethyl, lower alkyl, $SO_n$lower alkyl, $SO_nCF_3$, $SO_n$phenyl or $SO_2NR^6R^7$;

$R^3$ is hydrogen, lower alkyl or lower alkanoyl;
$R^4$ is $SO_nR^5$ or $SO_2NR^6R^7$;
n is 0, 1 or 2;
$R^5$ is

or trifluoromethyl; and $R^6$ and $R^7$ are hydrogen or lower alkyl or a pharmaceutically acceptable acid addition salt thereof.

2. A compound of claim 1 in which $R^3O$ is in the 8-position.

3. A compound of claim 1 in which $R^3O$ is in the 8-position and $R^4$ is in the 7-position.

4. A compound of claim 1, 2, or 3 in which $R^1$ is hydrogen or methyl, $R^2$ is hydrogen, hydroxy, $SO_n$-lower alkyl, $SO_nCF_3$, $SO_n$phenyl or $SO_nNR^6R^7$, $R^3$ is hydrogen and $R^4$ is $SO_nR^5$ or $SO_2NH_2$.

5. A compound of claim 1 said compound being 8-hydroxy-3-methyl-1-phenyl-7-phenylthio-2,3,4,5-tetrahydro-1H-3-benzazepine.

6. A compound of claim 1 said compound being 8-hydroxy-1-phenyl-7-trifluoromethylsulfonyl-2,3,4,5-tetrahydro-1H-3-benzazepine.

7. A compound of claim 1 said compound being 8-hydroxy-1-phenyl-7-sulfamoyl-2,3,4,5-tetrahydro-1H-3-benzazepine.

8. A pharmaceutical composition for treatment of gastrointestinal motility disorders comprising a pharmaceutical carrier and, in an amount sufficient to produce said activity, a compound of claim 1.

9. A method of treating gastrointestinal motility disorders which comprises administering internally to a subject in need of said treatment an effective amount of a compound of claim 1.

10. A method of claim 9 in which gastroesophageal reflux disease or delayed gastric emptying is treated.

* * * * *

UNITED STATES PATENT AND TRADEMARK OFFICE
CERTIFICATE OF CORRECTION

PATENT NO. : 4,707,483
DATED : November 17, 1987
INVENTOR(S) : William E. Bondinell, et al.

It is certified that error appears in the above-identified patent and that said Letters Patent is hereby corrected as shown below:

Column 3, 3rd structure: "$R^2SO_n\setminus$" should be -- $R^5SO_n\setminus$ -- .

Signed and Sealed this

First Day of November, 1988

Attest:

DONALD J. QUIGG

Attesting Officer

Commissioner of Patents and Trademarks